United States Patent [19]

Takashima

[11] Patent Number: 5,339,819

[45] Date of Patent: Aug. 23, 1994

[54] PULSE DETECTING APPARATUS

[75] Inventor: Mitsuru Takashima, Tokyo, Japan

[73] Assignee: Sony Corporation, Japan

[21] Appl. No.: 150,270

[22] Filed: Nov. 10, 1993

Related U.S. Application Data

[63] Continuation of Ser. No. 740,595, Aug. 5, 1991, abandoned.

[30] Foreign Application Priority Data

Aug. 22, 1990 [JP] Japan .................................. 2-218956

[51] Int. Cl.$^5$ ............................................. A61B 5/022
[52] U.S. Cl. ..................................... 128/681; 128/683
[58] Field of Search ............................ 128/681–683, 128/688, 680,

[56] References Cited

U.S. PATENT DOCUMENTS

| | | | |
|---|---|---|---|
| 4,458,690 | 7/1984 | O'Connor | 128/681 |
| 4,862,895 | 9/1989 | Yamasawa et al. | 128/680 |
| 4,880,013 | 11/1989 | Chio | 128/681 |
| 4,922,918 | 5/1990 | Ruiter | 128/681 |
| 5,103,831 | 4/1992 | Niwa | 128/672 |
| 5,170,795 | 12/1992 | Ramsey | 128/682 |

FOREIGN PATENT DOCUMENTS

| | | | |
|---|---|---|---|
| 0333449 | 9/1989 | European Pat. Off. | 128/680 |
| 0334652 | 9/1989 | European Pat. Off. | |
| 0335179 | 10/1989 | European Pat. Off. | 128/680 |
| 3606602 | 9/1986 | Fed. Rep. of Germany | |
| 7714246 | 6/1978 | Netherlands | 128/680 |

*Primary Examiner*—David H. Willse
*Attorney, Agent, or Firm*—Ronald P. Kananen

[57] ABSTRACT

A pulse detecting apparatus includes a combination of a pressure sensor; a minimum value detecting circuit for detecting a minimum value of the output of the pressure sensor; a maximum value detecting circuit for detecting a maximum value of the output of said pressure sensor; pressure applying member for biasing the a pressure sensor upon an artery; a static pressure sensor for detecting the biasing pressure to bias the pressure sensor of the pressure applying means upon the artery; and measured pressure detecting circuit for detecting based upon the output of the static pressure sensor the biasing pressures of said pressure applying member corresponding to the minimum and maximum value detected by said minimum and maximum values detecting means, respectively when the biasing pressure of the pressure applying member is decreased from a given value. A biasing pressure for biasing the pressure sensor of the pressure applying member upon the artery at which pulses necessary for the sphygmic diagnosis can be obtained, that is, the measured pressure, can be accurately determined.

3 Claims, 4 Drawing Sheets

PULSE DETECTING APPARATUS

This application is a continuation of application Ser. No. 07/740,595 filed Aug. 5, 1991, now abandoned.

BACKGROUND OF THE INVENTION

1. Field of the Invention

The present invention relates to a pulse detecting apparatus which detects arterial pulses by means of a pressure sensor.

2. Related Art

In oriental medicine, the conditions of a patient are determined by sphygmic diagnosis solely relying on the sense of touch of the arterial pulses on the "sunko", that is, the processus styloideus radii in the inner side of the wrist. In the sphygmic diagnosis of the oriental medicine, the pulses on the "sunko" are classified into those on three spots, such as upper, middle and lower spots which are referred to as "shun", "khan" and "shaku" and two kinds of pulsation condition "myakki" on the pulse route "keimyaku" appeared on respective spots are sensed.

The term "shun" means the distal end side of the artery of the wrist. The pulses on the "shun" represent the health conditions of a patient from the head to the chest. The term "khan" means the middle artery of the wrist between the distal end and the heart. The pulses on the "khan" represent the health conditions between the chest and the navel. The term "shaku" means the heart side of the artery in the wrist and the pulses on the "shaku" represents the health conditions between the navel and the toe.

A sphygmic diagnosis apparatus in which arterial pulses are detected from the artery of a human being by means of sensors such as an infrared ray sensor or a pressure sensor for performing the diagnosis by observation of the sphygmogram has heretofore been known as is disclosed in the specification of the Japanese Examined Patent Publication No. Sho 57-52054.

The disclosed diagnosis apparatus comprises three pressure sensors 61, 62 and 63, each including, for example, a piezoelectric microphone, for converting the arterial pulses on the three spots such as "shun", "khan", and "shaku" of the "sunko" into electrical signal waves and a cuff band 65 which is mounted on the wrist 64 of a patient for biasing the pressure sensors 61, 62 and 63 upon the artery of the wrist as shown in FIG. 5.

The pressure sensors 61, 62 and 63 are disposed on the wrist 64, that is, on and along the artery above the radius and the cuff 65 is wrapped around the wrist. Compressed air is pumped into an air bag (not shown) provided on the cuff 65 from a pneumatic pump via a conduit 66. Changes in arterial pulses can be measured by adjusting the amount of the pumped air to change the pressure applied upon the artery (hereafter referred to as "measured pressure").

The pressure sensors 61, 62 and 63 are connected with an electromagnetic oscillograph and the like through connection codes 61a, 62a and 63a, respectively so that the measured arterial pulses are recorded on a recording paper for observing the sphygmogram.

A pressure at which the blood begins to flow (hereinafter referred to as "high measured pressure" after the blood flow has been blocked by strongly biasing the pressure sensors upon the artery above the radius by pumping a lot of air into the air bag and the biasing pressure is gradually decreased is referred to as "chin" in the oriental medicine and a pressure immediately before the pulses do not occur hereinafter referred to as low measured pressure) when the biasing pressure is further decreased is referred to as "fu" in the oriental medicine. The pulses at these "chin" and "fu" are required for sphygmic diagnosis. However, although the prior art pulse detecting apparatus is capable of detecting the pulses for all biasing pressures when the biasing pressure upon the artery is changed, it does not have means for determining the pulses necessary for sphygmic diagnosis, that is, the pulses at "chin" and "fu". The pulses at "chin" and "fu" are determined based on experience. Therefore, there is a problem that experiences are required for diagnose the illness by the sphygmic diagnosis.

The present invention was made under such circumstances. It is an object of the present invention to provide a pulse detecting apparatus which is capable of obtaining the accurate measured pressures, from which pulses necessary for the pulse diagnosis can be obtained, that is the values of "chin" and "fu".

OBJECT AND SUMMARY OF THE INVENTION

In order to accomplish the above-mentioned object, the present invention provides a pulse detecting apparatus, comprising; a pressure sensor; a minimum value detecting means for detecting a minimum value of the output of said pressure sensor; a maximum value detecting means for detecting a maximum value of the output of said pressure sensor; pressure applying means for biasing said pressure sensor upon the artery; a static pressure sensor for detecting the biasing pressure to bias said pressure sensor of said pressure applying means upon the artery; and measured pressure detecting means for detecting based upon the output of said static pressure sensor the biasing pressures of said pressure applying means corresponding to the minimum and maximum values detected by said minimum and maximum values detecting means, respectively, when the biasing pressure of the pressure applying means is decreased from a given value.

Operation

In the pulse detecting apparatus of the present invention, biasing pressures of the biasing means corresponding to minimum and maximum values detected by the minimum and maximum value detecting means, respectively are outputted as measured pressures, from which pulses necessary for sphygmic diagnosis can be obtained.

DESCRIPTION OF THE EMBODIMENTS

Now, a first embodiment of the present invention will be described with reference to the drawings.

Figure 1:
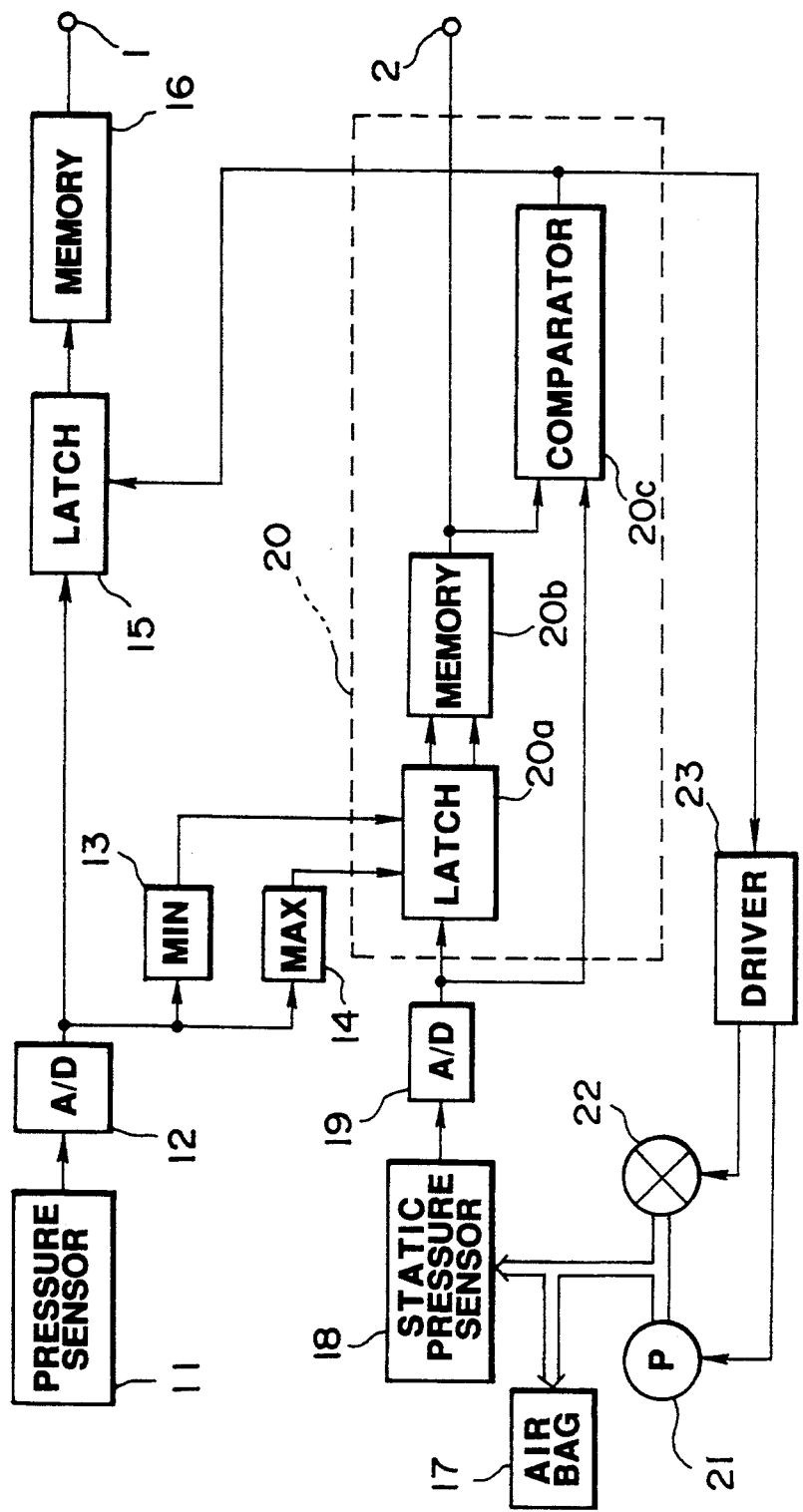
FIG. 1 is a block diagram of a first embodiment of a pulse detecting apparatus of the present invention.

The pulse detecting apparatus of the first embodiment is adapted to obtain arterial pulse information by detecting as changes in pressure, arterial pulses in three spots such as "shun", "khan", and "shaku" of the "sunko" which are referred in the oriental medicine. FIG. 1 is a block diagram of a part of the pulse detecting apparatus for detecting for example, the "shaku" in the "sunko", that is, the arterial pulses in the heart side and for detecting the measured pressure to detect pulses necessary for sphygmic diagnosis. In other words, the pulse detecting apparatus has circuits (not shown) for detecting other arterial pulses in "shun" and "khan" of the "sunko" which are identical to the circuit for detecting pulses in the "shaku" of the "sunko".

The pulse detecting apparatus comprises a pressure sensor 11 for detecting the arterial pulses in, for example, the "shun" of the "sunko", a minimum value detecting circuit 13 for detecting a minimum value of an output from the pressure sensor 11, a maximum value detecting circuit 14 for detecting a maximum value of an output from the pressure sensor 11, an air bag 17 for biasing the pressure sensor 11 upon the artery, a static pressure sensor 18 for detecting the pressure of the air bag 17, a measured pressure detecting circuit 20 for detecting the values of said static pressure sensor 18 corresponding to the above-mentioned "fu" and "chin" to output them as measured pressures.

The pressure sensor 11 comprises a pressure-mechanical transducing element such as piezo-electric microphone and detects as changes in pressure the arterial pulses in the "shaku" of the "sunko" as mentioned above. The output of the pressure sensor 11 is converted into digital data (hereinafter referred to as pulse data) by an a/d converting circuit 12 and fed to the minimum value detecting circuit 13, the maximum value detecting circuit 14 and a latch circuit 15. After the pulse data has been once latched by the latch circuit 15 in response to a clock from the measured pressure detecting circuit 20, it is stored in a memory circuit 16. The pulse data which has been stored in the memory circuit 16 will be outputted from terminal 1 as a pulse data of the "shaku" of the "sunko" necessary for sphygmic diagnosis.

The minimum value detecting circuit 13 detects a minimum value of the pulse data from the a/d converting circuit 12 and supplies a clock to the measured pressure detecting circuit 20 whenever a maximum value is newly detected.

The air bag 17 is connected with the static pressure sensor 18, a pneumatic pump 21 and a leak valve 22 through a conduit and the like. By controlling the pneumatic pump 21 and the leak valve 22 to introduce the air into the air bag 17 from the pneumatic pump 21, the pressure sensor 11 is biased upon the artery. The biasing pressure of the pressure sensor 11 applied upon the artery is gradually decreased by gradually leaking the air from the leak valve 22.

The static pressure sensor 18 comprises, for example, a piezoelectric microphone and is adapted to detect the inner pressure of the air bag 17, that is, the biasing pressure of the pressure sensor 11 applied upon the artery. The output of the static pressure sensor 18 is converted into digital data (hereinafter referred to as "static pressure data") by the a/d converting circuit 19 and is fed to the measure pressure detecting circuit 20.

The measured pressure detecting circuit 20 comprises a latch circuit 20a, a memory circuit 20b and a comparator circuit 20c. The static pressure data from the a/d converting circuit 19 is fed to the latch circuit 20a and the comparator circuit 20c. After the static pressure data has been latched by the latch circuit 20a in response to a clock from the minimum value detecting circuit 13 and the maximum value detecting circuit 14, it is stored in the memory circuit 20b. The static pressure data stored in the memory circuit 20b is outputted from a terminal 2 as a measured pressure data. The comparator circuit 20c compares the measured pressure data stored on the memory circuit 20b with the static pressure data from the a/d converting circuit 19 and supplies the latch circuit 15 and the driver circuit 23 with a clock when both data are equal.

A portion of the pulse detecting apparatus mounted on the wrist will be briefly described.

Figure 2:
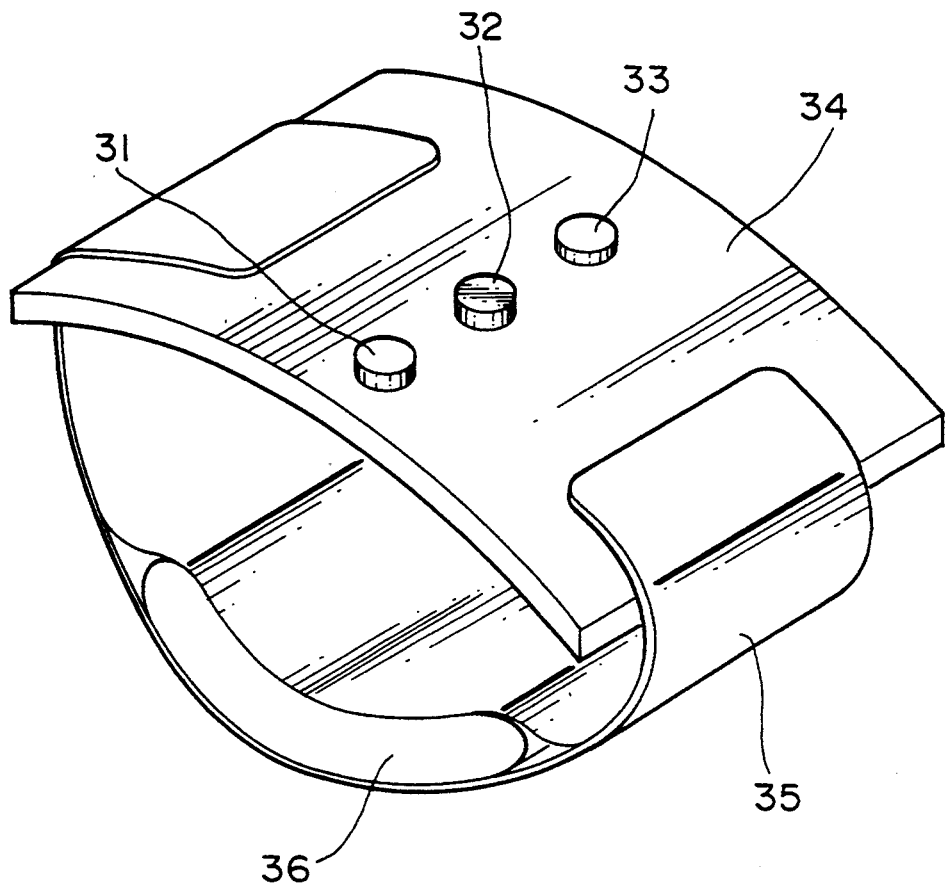
FIG. 2 is a perspective view showing a part of the pulse detecting apparatus which is mounted on the wrist.

The portion of the pulse detecting apparatus mounted upon the wrist is adapted to detect arterial pulses in three spots such as "shun", "khan", and "shaku" of the "sunko" as mentioned above and comprises three pressure sensors 31, 32 and 33 for detecting arterial pulse, a mounting plate 34 on which the pressure sensors 31, 32 and 33 are mounted, a cuff 35 linked to the both ends of the mounting plate 34 so that the side of the plate on which the pressure sensors 31, 32 and 33 are mounted is located inside thereof, and the air bag 36 disposed on the cuff 35 so that the bag faces to the pressure sensors 31, 32 and 33 as shown in FIG. 2. The pressure sensor 33 and the air bag 36 correspond to the pressure sensor 11 and the air bag 17 shown in FIG. 1, respectively.

The three pressure sensors 31, 32 and 33 detect as changes in pressure the arterial pulses in three positions such as "shun", "khan" and "shaku" of the "sunko", respectively and comprise, for example, a piezoelectric microphone.

The mounting plate 34 has a curvature in a direction of the artery of the carpus in position of the "sunko", the processus styloideus radii, which is larger than that in a vertical direction. The pressure sensors 31, 32 and 33 are disposed inside of the mounting plate 34 so that the sensors are positioned correspondingly on the three spots such as "shun", "khan", "shaku" of the "sunko", respectively. The mounting plate 34 is made of, for example, a transparent member having a rigidity so that the mounting positions of the pressure sensors 31, 32 and 33 are visually observed (by eyes) from the outside of thereof.

The cuff 35 is linked to the mounting plate 34 at one end thereof by means of, for example, a bonding agent. On the other hand, the cuff 35 is detachably linked to the mounting plate 34 at the other end thereof by means of, for example, a velcro tape so that a hand can be freely inserted between the mounting plate 34 and the air bag 35.

The air bag 36 is connected to a pneumatic pump (not shown) via a conduit as mentioned above and is adapted to press the back of the wrist to bias the pressure sensors 31, 32 and 33 upon the artery on three spots, such as "shun", "khan", and "shaku" of the "sunko" at a predetermined pressure.

In order to detect the pulses, a wrist is inserted between the mounting plate 34 and the air bag 36 and air is pumped into the air bag 36, the positions of the pressure sensors 31, 32 and 33 relative to the artery positioned above the radius are visually observed through the mounting plate 34. The pressure sensors 31, 32 and 33 are biased upon the artery positioned above the radius so that they are exactly positioned thereon. Outputs from the pressure sensors 31, 32 and 33 are thus obtained.

Now, operation of the pulse detecting apparatus having the circuit shown in FIG. 1 will be described.

Firstly, air is pumped into the air bag 17 from the pneumatic pump 21 until the biasing pressure upon the pressure sensor 11 becomes a predetermined value, such as a pressure for blocking the blood flow (hereinafter referred to as "blood flow blocking pressure"). Then, the air is gradually leaked from the air bag 17 through the leak valve 22 to decrease the biasing pressure.

Figure 3:
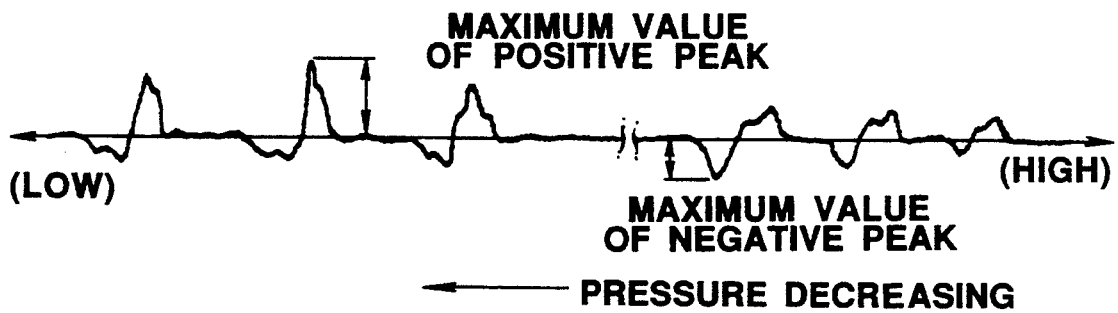
FIG. 3 is a chart showing the wave form of the pulses detected by a pressure sensor when the biasing pressure of the pressure sensor is gradually decreased.

At this time, the pressure sensor 11 detects the pulses, the amplitude of which increases as the pressure decreases as shown in FIG. 3. The pulses reach a negative maximum peak value and thereafter reach a positive peak value with decrease in the pressure. The pulses are not detected after the pressure is further decreased.

Accordingly, when the biasing pressure is gradually decreased from the blood flow blocking pressure, a minimum value detecting circuit 13 applies a clock to a latch circuit 20a every time when a minimum value is newly detected. A maximum value detecting circuit 14 applies a clock to the latch circuit 20a every time when a maximum value is newly detected. As a result of this, two static data (hereinafter referred to as "high and low measured pressure data") from the static sensor 18 corresponding to the maximum values of the negative and positive peaks, respectively, are latched by the latch circuit 20a. The measured pressure data are stored in a memory circuit 20b. That is, the measured pressure data corresponding to the above-mentioned "chin" and "fu" are stored in the memory circuit 20b.

The pressure is then gradually decreased after the pressure biasing the pressure sensor 11 is increased to the blood flow blocking pressure. Current static pressure data detected by the static pressure sensor 18 is compared with the high and low measured pressure data stored in the memory circuit 20b by a comparator circuit 20c. The comparator circuit 20c feeds a clock to the latch circuit 15 and the driver circuit 23 when the current static pressure is equal to high or low measured pressure data.

Pulse data of, for example, one beat detected by the pressure sensor 11 is latched by the latch circuit 15 in response to the clocks. As a result of this, respective pulse data of one pulse corresponding to high and low measured pressure data are latched. The latched data are stored in the memory circuit 16. The driver circuit 23 may change the pressure of the air bag 17 in the vicinity of high and low measured pressure data by controlling the pneumatic pump 21 and the leak valve 22 in response to the clocks from the comparator circuit 20c. The pulse data of one beat corresponding to high and low measured pressure data may be positively latched by the latch circuit 15.

The two measured pressure data stored in the memory circuit 20b are outputted from the terminal 2 as measured pressures ("chin" and "fu"). The pulse data stored in the memory circuit 16 are outputted from the terminal 1 as pulse data of the "shaku" of the "sunko" necessary for sphygmic diagnosis.

Similarly, pulse data or the "shun" and the "khan" necessary for the sphygmic diagnosis are detected by and outputted from the pressure sensors (not shown) for the "shun" and the "khan" of the "sunko".

In accordance with the present embodiment, measured pressures, from which pulses necessary for the sphygmic diagnosis can be obtained, that is, the values of "chin" and "fu" can be accurately determined by detecting, based upon the outputs of the static pressure sensor 18, the biasing pressures of the air bag 17 corresponding to the maximum and minimum values detected by the maximum and minimum value detecting circuits 14 and 13, respectively when the biasing pressure of the pressure sensor 11 of the air bag 17 upon the artery is decreased from the blood flow blocking pressure.

A second embodiment of the present invention will be described.

Figure 4:
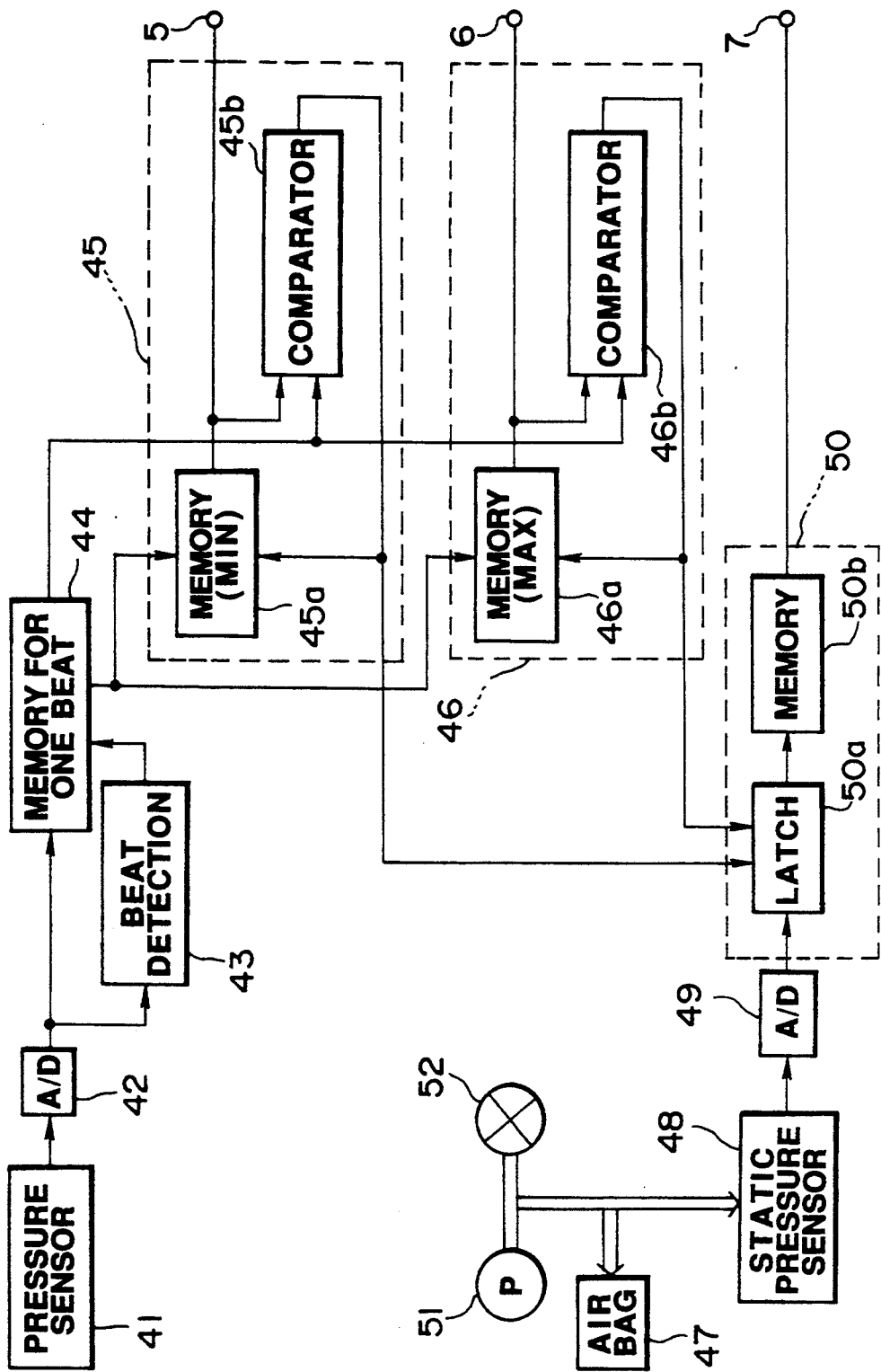
FIG. 4 is a block diagram showing a second embodiment of a pulse detecting apparatus of the present invention.
Figure 5:
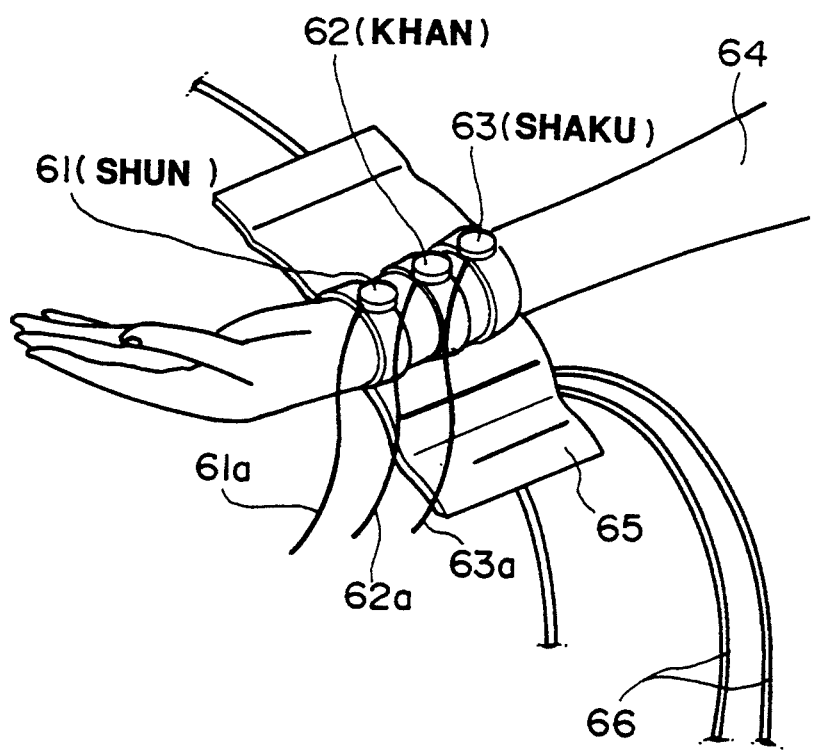
FIG. 5 is a perspective view showing a part of the pulse detecting apparatus which is mounted on the wrist.

A pulse detecting apparatus of the second embodiment is adapted to detect as pressure changes arterial pulses on three spots, such as "shun", "khan" and "shaku" of the "sunko" defined by oriental medicine to obtain arterial pulse information, similar to the foregoing first embodiment. FIG. 4 is a block diagram showing a part of a pulse detecting apparatus for detecting the arterial pulses on the "shaku" of the "sunko", that is, the arterial pulses in the heart side and for detecting the measured pressures from which pulses necessary for sphygmic diagnosis can be determined. That is, the pulse detecting apparatus has circuits (not shown) for detecting the other arterial pulses on the "shun" and "khan" of the "sunko" having the structure identical with that of the circuit for detecting the pulses on the "shaku" of the "sunko".

The difference between the first and second embodiments resides in that in the first embodiment after a measured pressure data has been obtained by decreasing the pressure from the blood flow blocking pressure, the pressure of the air bag is increased to the blood flow blocking pressure and pulse data is obtained in the course of the second pressure decreasing process while in the second embodiment both measured pressure data and pulse data are obtained in one pressure decreasing process.

Specifically, as shown in FIG. 4, the pulse detecting apparatus comprises one of the above mentioned three pressure sensors, for example, a pressure sensor 41 for detecting the arterial pulses on the "shaku" of the "sunko", a heart beat detecting circuit 43 for detecting the heart beat from the output of the pressure sensor 31 to generate clocks in synchronization with the heart beat, a memory circuit 44 for storing pulse data of one beat based upon the clocks from the heart beat detecting circuit 43, a minimum value detecting circuit 45 for detecting a minimum value of an output from the pressure sensor 41 based upon the pulse data from the memory circuit 44, a maximum value detecting circuit 46 for detecting a maximum value of an output from the pressure sensor 41 based upon the pulse data from the memory circuit 44, an air bag 47 for pressing the pressure sensor 41 upon the artery, a static pressure sensor 48 for detecting the pressure of the air bag 47, a measured pressure detecting circuit 50 for detecting the values of said static pressure sensor 48 corresponding to the above-mentioned "fu" and "chin" to output them as measured pressures.

The pressure sensor 41 comprises a pressure-mechanical transducing element, such as a piezo-electric microphone, and detects as changes in pressure the arterial pulses in the shaku of the "sunko" as mentioned above. The output of the pressure sensor 41 is converted into digital data (hereafter referred to as "pulse data") by an a/d converting circuit 42 and is fed to the minimum value detecting circuit 45, and the maximum value detecting circuit 46.

The minimum value detecting circuit 45 comprises a memory circuit 45a for storing pulse data of one beat and a comparator circuit 45b. The pulse data from the memory circuit 44 are supplied to the memory circuit 45a and the comparator circuit 45b and are stored in the memory circuit 45a in response to the clocks from the comparator circuit 45b. The comparator circuit 45b compares the pulse data from the memory circuit 44 with the pulse data stored in the memory circuit 45a and supplies a clock to the memory circuit 45a and the measured pressure detecting circuit 50 when the pulse data from the memory circuit 44 is lower. The pulse data stored in the memory circuit 45a is outputted from a terminal 5 as the pulse data of the "shaku" of the "sunko" necessary for the sphygmic diagnosis.

The minimum value detecting circuit 46 comprises memory circuit 46a for storing pulse data of one beat and a comparator circuit 46b. The pulse data from the memory circuit 44 are supplied to the memory circuit 46a and the comparator circuit 46b and stored in the memory circuit 46a in response to the clocks from the comparator circuit 46b. The comparator circuit 46b compares the pulse data from the memory circuit 44 with the pulse data stored in the memory circuit 46a and supplies a clock to the memory circuit 46a and the measured pressure detecting circuit 50 when the pulse data from the memory circuit 44 is higher. The pulse data stored in the memory circuit 46a is outputted from a terminal 6 as the pulse data of the "shaku" of the "sunko" necessary for the sphygmic diagnosis.

The air bag 47 is connected with the static pressure sensor 48, a pneumatic pump 51 and a leak valve 52 through a conduit and the like. By controlling the pneumatic pump 51 and the leak valve 52 to introduce the air into the air bag 47 from the pneumatic pump 51, the pressure sensor 41 is biased upon the artery. The biasing pressure of the pressure sensor 41 applied upon the artery is gradually decreased by gradually leaking the air from the leak valve 52.

The static pressure sensor 48 comprises, for example, a piezoelectric microphone and is adapted to detect the inner pressure of the air bag 47, that is, the biasing pressure of the pressure sensor 41 applied upon the artery. The output of the static pressure sensor 48 is converted into digital data (hereinafter referred to as "static pressure data") by the a/d converting circuit 49 and is fed to the measured pressure detecting circuit 50.

The measured pressure detecting circuit 50 comprises a latch circuit 50a and a memory circuit 50b. The static pressure data from the a/d converting circuit 49 is fed to the latch circuit 50a. After the static pressure data has been latched by the latch circuit 50a in response to each clock from the minimum value detecting circuit 45 and the maximum value detecting circuit 46, it is stored in the memory circuit 50b. The static pressure data stored in the memory circuit 50b is outputted from terminal 7 as a measured pressure data.

Now, operation of the pulse detecting apparatus having the circuit shown in FIG. 4 will be described.

Firstly, air is pumped into the air bag 41 from the pneumatic pump 51 until the biasing pressure upon the pressure sensor 41 becomes a predetermined value, such as a pressure for blocking the blood flow (hereinafter referred to as "blood flow blocking pressure"). Then, the air is gradually leaked from the air bag 47 through the leak valve 52 to decrease the biasing pressure.

At this time, the pressure sensor 41 detects the pulses, the amplitude of which increases as the pressure decreases as shown in FIG. 3. The pulses reach a negative maximum peak value and thereafter reach a positive peak value with decrease in the pressure. The pulses are not detected after the pressure is further decreased.

Accordingly, when the biasing pressure is gradually decreased from the blood flow blocking pressure, a comparator circuit 45b applies a clock to a memory circuit 45a and a latch circuit 50a every time when a minimum value is newly detected. A comparator circuit 46b applies a clock to the memory circuit 46 and the latch circuit 50a every time when a maximum value is newly detected. As a result of this, two static data (hereinafter referred to as high and low measured pressure data) from the static sensor 48 corresponding to the maximum values of the negative and positive peaks, respectively, are latched by the latch circuit 50a. The measured pressure data are stored in a memory circuit 50b. The pulse data of one beat corresponding to the high measured pressure data is stored in the memory circuit 45a. The pulse data of one beat corresponding to the low measured pressure data is stored in the memory circuit 46a. That is, the measured data corresponding to the above-mentioned "chin" and "fu" are stored in the memory circuit 50a. The pulse data corresponding to the high and low measured pressure are stored in the memory circuit 45a and 46a, respectively.

The measured pressure data stored in the memory circuit 50b is outputted from a terminal 7 as a measured pressure and the pulse data stored in the memory circuits 45a and 46a are outputted from the terminals 5 and 6, respectively, as pulse data of the shaku of the sunko necessary for the sphygmic diagnosis.

Similarly, pulse data of the "shun" and "khan" necessary for the sphygmic diagnosis are detected by and outputted from the pressure sensors (not shown) for the "shun" and the "khan" of the "sunko".

In accordance with the present embodiment, measured pressures, from which pulses necessary for the sphygmic diagnosis can be obtained, that is, the values of "chin" and "fu" can be accurately determined by detecting based upon the outputs of the static pressure sensor 48 the biasing pressures of the air bag 47 corresponding to the maximum and minimum values detected by the maximum and minimum value detecting circuits 46 and 45, respectively, when the biasing pressure of the pressure sensor 41 of the air bag 47 upon the artery is decreased from the blood flow blocking pressure.

As is apparent from the fore-going description, in the present invention, the pressure sensors for detecting the arterial pulses on the "sunko" are biased upon the artery by means of pressure applying means such as an air bag and the biasing pressure is detected by the static sensor. By detecting the biasing forces of the pressure applying means corresponding to minimum and maximum values of the output of the pressure sensors based upon the output of the static pressure sensor when the biasing pressure of the pressure applying means is decreased from, for example, a blood flow blocking pressure, measured pressures, from which pulses necessary for sphygmic diagnosis, that is, the values of "chin" and "fu" can be obtained can be accurately determined.

What is claimed is:

1. A pulse detecting apparatus, comprising:

a first pressure sensor;

a minimum value detecting means for detecting a minimum value of the output of said first pressure sensor;

a maximum value detecting means for detecting a maximum value of the output of said first pressure sensor;

pressure applying means for biasing said first pressure sensor upon an artery;

a second pressure sensor for detecting a static biasing pressure to bias said first pressure sensor of said pressure applying means upon the artery; and measured pressure detecting means for detecting, based upon the output of said second pressure sensor, the biasing pressures of said pressure applying means corresponding to the minimum and maximum values detected by said minimum and maximum value detecting means, respectively, when the biasing pressure of the pressure applying means is decreased from a given value, said measured pressure detecting means including means for storing output values of said second pressure sensor representative of the biasing pressures of said pressure applying means obtained at a first time period when minimum and maximum values are detected by said minimum and maximum value detecting means, respectively, and further including comparing means for comparing the respective values stored in said storing means at said first time with the outputs from said second pressure sensor obtained at a second time period, said second time period corresponding to a period occurring when the biasing pressure of said pressure applying means is decreased again from the given value increased by said pressure applying means and after the output values of said second pressure sensor obtained during said first time period have been stored in said storing means of said measured pressure detecting means; and pulse data recording means for storing detected outputs of said first pressure sensor corresponding to one heart beat, said detected outputs stored in said data recording means indicating values at a period at which the comparing means determines that an output value of said second pressure sensor at said first time period is equal to the corresponding output value of said second pressure sensor at said second time period.

2. A pulse detecting apparatus, comprising:

a first pressure sensor;

a minimum value detecting means for detecting a minimum value of the output of said first pressure sensor;

a maximum value detecting means for detecting a maximum value of the output of said first pressure sensor;

pressure applying means for biasing said pressure sensor upon an artery;

a second pressure sensor for detecting a static biasing pressure to bias said pressure sensor of said pressure applying means upon the artery; and measured pressure detecting means for detecting, based upon the output of said second pressure sensor, the biasing pressures of said pressure applying means corresponding to the minimum and maximum values detected by said minimum and maximum value detecting means, respectively, when the biasing pressure of the pressure applying means is decreased from a given value, and further including heart beat detecting means for detecting beats of a heart from the detected outputs of said first pressure sensor;

wherein said measured pressure detecting means further includes a first storing means for storing pulse data which are detected outputs from said first pressure sensor based upon the detected outputs from said heart beat detecting means, said pulse data being stored for a period of one heart beat;

wherein said maximum value detecting means includes second storing means to which the outputs of said first storing means are transferred and first comparing means for comparing the outputs from said second storing means with the outputs from said first storing means; and wherein said minimum value storing means includes third storing means to which the outputs from said first storing means are transferred and second comparing means for comparing the outputs from said third storing means with the outputs from said first storing means.

3. A pulse detecting apparatus as defined in claim 2 in which said measured pressure detecting means includes means for storing the outputs of said second pressure sensor representative of biasing pressures of said pressure applying means corresponding to minimum and maximum values detected by said minimum and maximum value detecting means, respectively.

* * * * *